United States Patent [19]
Moe

[11] Patent Number: 6,117,169
[45] Date of Patent: *Sep. 12, 2000

[54] LIVING HINGE ATTACHMENT OF LEAFLET TO A VALVE BODY

[75] Inventor: Riyad E. Moe, Austin, Tex.

[73] Assignee: Sulzer Carbomedics Inc., Austin, Tex.

[*] Notice: This patent issued on a continued prosecution application filed under 37 CFR 1.53(d), and is subject to the twenty year patent term provisions of 35 U.S.C. 154(a)(2).

[21] Appl. No.: 09/103,483

[22] Filed: Jun. 24, 1998

[51] Int. Cl.$^7$ ........................................ A61F 2/24
[52] U.S. Cl. ........................... 623/2.12; 623/2.1
[58] Field of Search ................... 623/2, 66, 900

[56] References Cited

U.S. PATENT DOCUMENTS

| | | | |
|---|---|---|---|
| 3,579,642 | 5/1971 | Heffernan et al. | 623/2 |
| 3,589,392 | 6/1971 | Meyer | 137/525.1 |
| 4,009,648 | 3/1977 | Braden et al. | 98/40 |
| 4,030,142 | 6/1977 | Wolfe | 3/1.5 |
| 4,178,638 | 12/1979 | Meyer | 3/1.5 |
| 4,204,283 | 5/1980 | Bellhouse et al. | 3/1.5 |
| 4,262,802 | 4/1981 | Laauwe | 206/540 |
| 4,263,680 | 4/1981 | Reul et al. | 3/1.5 |
| 4,556,996 | 12/1985 | Wallace | 623/2 |
| 4,643,732 | 2/1987 | Pietsch et al. | 623/2 |
| 4,778,461 | 10/1988 | Pietsch et al. | 623/2 |
| 5,078,739 | 1/1992 | Martin | 623/2 |
| 5,116,564 | 5/1992 | Jansen et al. | 264/255 |
| 5,258,023 | 11/1993 | Reger | 623/2 |
| 5,376,113 | 12/1994 | Jansen et al. | 623/2 |
| 5,405,381 | 4/1995 | Olin | 623/2 |
| 5,439,143 | 8/1995 | Brown et al. | 222/185 |
| 5,469,868 | 11/1995 | Reger | 128/898 |
| 5,500,016 | 3/1996 | Fisher | 623/2 |
| 5,728,976 | 3/1998 | Santucci et al. | 174/135 |

OTHER PUBLICATIONS

"Polyurethane Artificial Heart Valves in Animals", Akutsu, Dreyer, Kolff; Unknown Publication; Unknown Date.

"Complete Replacement of the Mitral Valve", Braunwald, Cooper, Morrow, J. Thoracic & Cardiovascular Surgery 40:1–11 (1960).

"Late Follow–up Studies on Flexible Leaflet Prosthetic Valves", Roe, J. Thoracic & Cardiovascular Surgery 58: 59–61 (1969).

(List continued on next page.)

*Primary Examiner*—Mickey Yu
*Assistant Examiner*—Alvin Stewart
*Attorney, Agent, or Firm*—Timothy L. Scott; Philip S. Lyren; Kenneth S. Barrow

[57] ABSTRACT

A valve including a living hinge coupling a leaflet to a valve body. The leaflet can be coupled through the living hinge to the valve body's inner diameter, its outer diameter, or somewhere between the two diameters. Because the living hinge design of the valve is an integrated part, it can be manufactured in a single step.

5 Claims, 7 Drawing Sheets

OTHER PUBLICATIONS

"Design and Durability Test of Silastic Trileaflet Aortic Valve Prostheses", Mohri, Hessel, Nelson, Anderson, Dillard, Merendino, J. Thoracic & Cardiovascular Surgery 65:576–582 (1973).

"Reflections on the Development of Valvular Prostheses", Hufnagel, J. Association Adv. Med. Instr. 11:74–76 (1977).

"A Polyurethane Trileaflet Cardiac Valve Prosthesis: In Vitro and In Vivo Studies", Wisman, Pierce, Donachy, Pae, Myers, Prophet; Trans. Am. Soc. Artif. Intern. Organs, 28:164–168 (1982).

"Evaluation of Explanted Polyurethane Trileaflet Cardiac Valve Prostheses", Hilbert, Ferrans, Tomita, Eidbo, Jones, J. Thoracic & Cardiovascular Surgery 94:419–429 (1987).

"Experimental Analysis of Mechanical Failure of Polyurethane Trileaflet Valve", Yu, Drevjin, Kolff, Proceedings of the 40th Annual Conference on Engineering in Medicine and Biology 117 (1987).

"New J–3 Flexible–Leaflet Polyurethane Heart Valve Prosthesis with Improved Hydrodynamic Performance", Jansen, Willeke, Reiners, Harbott, Reul, Rau, Int'l J. of Artificial Organs 14:655–660 (1991).

"Stress Distribution on the Cusps of a Polyurethane Trileaflet Heart Valve in the Closed Position", Chandra, Kim, Han, J. Biomedics 24:385–395 (1991).

"A Synthetic Three–leaflet Valve", Jansen, Ruel, J. of Medical Engineering & Technology 16:27–33 (1992).

"Elastomeric Valves, A New Design", Hulsbergen, Topaz, Kumar, Bishop, Shelton, Granger, Chiang, Boer, Luikenaar, Mohammed, kolff, Int'l J. of Artificial Organs 18:203–209 (1995).

"In Vitro Function and Durability Assessment of a Novel Polyurethane Heart Valve Prosthesis", Mackay, Bernacca, Fisher, Hindle, Wheatley, Artificial Organs 20:1017–1025 (1996).

"The Influence of Open Leaflet Geometry on the Haemodynamic Flow Characteristic of Polyurethane Trileaflet Heart Valves", Proc. Instn. Mech. Engrs., 210:273–287 (1996).

"On Stress Reduction in Bioprosthetic Heart Valve Leaflets by the Use of a Flexible Stent", Christie, Barratt–Boyles, J. of Cardiac Surgery 6:476–481 (1991).

"Stress–Related Failure Modes of Bovine Pericardial Heart Valves", Christie, Stephenson, Surgery for Heart Valve Disease; unknown publication, unknown date.

"Finite Element Stress Analysis of a New Design of Synthetic Leaflet Heart Valve", Clift, Fisher, Proc. Instn. Mech. Engrs. 210:267–272 (1996).

"The Bovine Pericardial Bioprosthetic Heart Valve: Methods for Tensile Stress Reduction in the Leaflets During the Loaded Phase", Christie, Advances in Bioengineering 20: 647–650 (1991).

LIVING HINGE ATTACHMENT OF LEAFLET TO A VALVE BODY

TECHNICAL FIELD

The present invention pertains to valves and in particular to polymer heart valve prostheses.

BACKGROUND OF THE PRIOR ART

Ever since 1950, when blood oxygenators made open heart surgery feasible, it has been possible to treat some forms of heart disease by replacing one of the patient's heart valves with a prosthetic valve. Early heart valve prostheses included ball-and-cage valves and disc-and-cage valves in which a ball or a disc was housed in a cage. One side of the cage provided an orifice through which blood flowed either into or out of the heart, depending on the valve being replaced. When blood flowed in a forward direction, the energy of the blood flow forced the ball or disc to the back of the cage allowing blood to flow through the valve. When blood attempted to flow in a reverse direction, or "regurgitate", the energy of the blood flow forced the ball or disc into the orifice in the valve and blocked the flow of blood.

A bi-leaflet valve comprised an annular valve body in which two opposed leaflet occluders were pivotally mounted. The occluders were typically substantially rigid, although some designs incorporated flexible leaflets, and moved between a closed position, in which the two leaflets were mated and blocked blood flow in the reverse direction, and an open position, in which the occluders were pivoted away from each other and did not block blood flow in the forward direction. The energy of blood flow caused the occluders to move between their open and closed positions.

A tri-leaflet valve comprised an annular valve body in which three flexible leaflets were mounted to a portion of the valve body, called a "stent," located at the circumference of the annulus. Some tri-leaflet valves used rigid leaflets. When blood flowed in the forward direction, the energy of the blood flow deflected the three leaflets away from the center of the annulus and allowed blood to flow through. When blood flowed in the reverse direction, the three leaflets engaged each other in a coaptive region, occluded the valve body annulus and prevented the flow of blood. The valve leaflets were made from tissue, such as specially treated porcine or bovine pericardial tissue, or, more recently, from a man-made material such as polyurethane or another biocompatible polymer.

Prosthetic heart valves should be reliable and durable because replacing a failed implanted valve is expensive and dangerous for the patient. Typically, the heart valve leaflets are the component most likely to fail. One of the factors that contributes to structural failure of heart valve leaflets is the level of stress leaflets experience in operation. Flexible membranes, such as heart valve leaflets, experience two kinds of stress. The first, called "membrane stress," is produced by the two-dimensional stretching of the membrane, and is linearly related to the pressure difference across the membrane (although the stress constants will vary due to curvature and thickness).

The second kind of stress, called "bending stress," is linearly related to the change in local curvature from the stress-free condition (although, again, the stress constants will vary according to the thickness of the membrane). The membrane stress and bending stress are superimposed to determine maximum stress. Lowering either type of stress will reduce maximum stress.

BRIEF SUMMARY OF THE INVENTION

A valve according to the invention reduces bending stress, and therefore the total stress, on the leaflet by incorporating a living hinge to couple the leaflet to the valve body. The living hinge coupling is provided between a coupling end of the leaflet and the valve body. The coupling is configured so that when a force is applied to the leaflet in a valve opening direction, the coupling end of the leaflet translates and rotates relative to the valve body. The coupling may be attached to the inner diameter or the outer diameter of the valve body, or it may be attached between the inner and outer diameters of the valve body. Because a leaflet and a valve body joined by a living hinge are a single integrated part, the valve can be manufactured in a single step using such manufacturing techniques as injection molding, dip casting, and thermoforming.

DETAILED DESCRIPTION OF THE INVENTION

Figure 1:
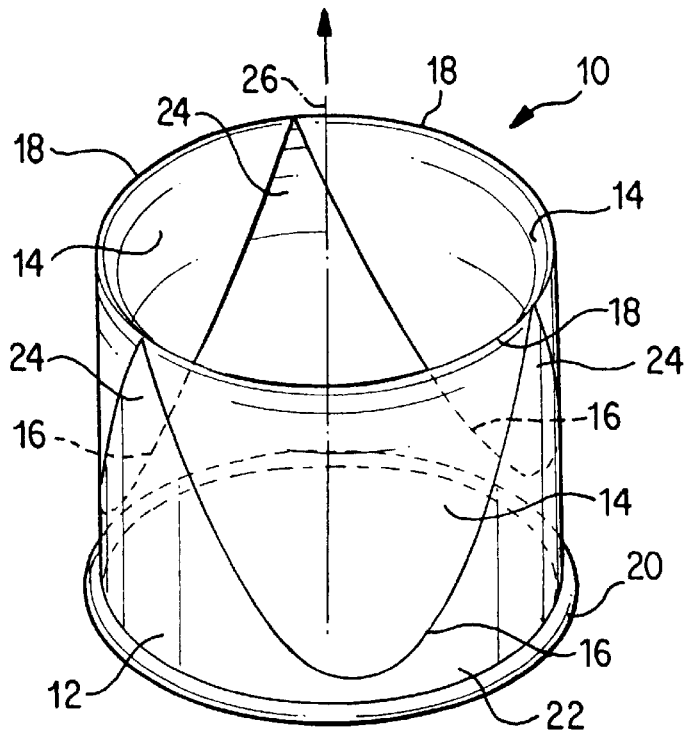
FIG. 1 is a perspective view of a tri-leaflet valve in the open position.

A tri-leaflet heart valve prosthesis 10 comprises an annular valve body 12 and three flexible leaflets 14 made of a biocompatible polymer such as silicone or polyurethane, as shown in FIG. 1. Each leaflet is coupled to the valve body along an attachment curve 16. Each leaflet has a free edge 18 that is not coupled to the valve body. A sewing ring 20 is coupled to the base of the valve body 12 and provides a place for sutures to be applied when the valve is implanted. The valve body comprises an annular base 22 and a leaflet support, comprising three shaped posts 24, that supports the leaflets 14.

Figure 2:
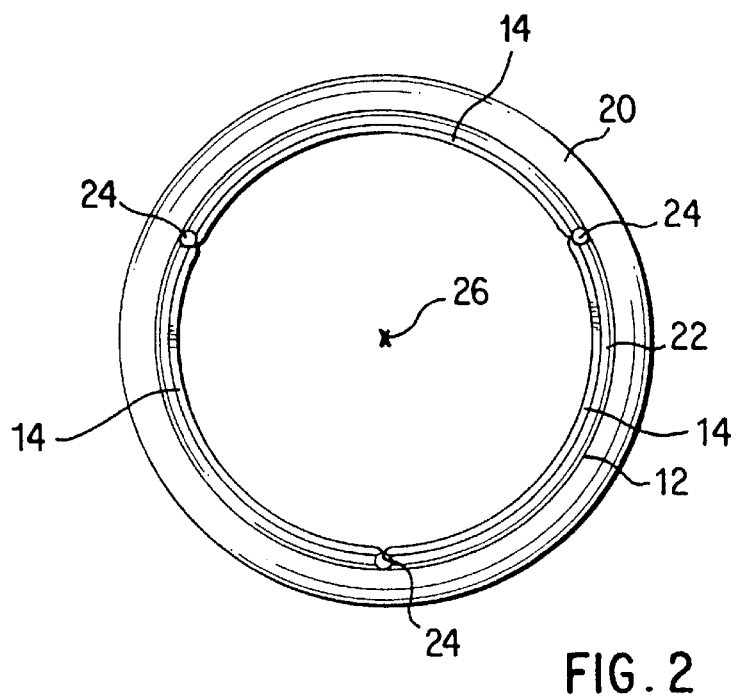
FIG. 2 is a plan view of the valve of FIG. 1.

When fluid flow is in the forward direction, i.e. in the direction of the arrow shown in FIG. 1, the pressure of the blood flow causes the leaflets 14 to deflect away from a central longitudinal axis 26 of the valve body that is generally parallel to the three posts 24. In this "open" position, the leaflets 14 define a large flow orifice, as shown in FIG. 2. With the leaflets in the open position shown in FIGS. 1 and 2, the valve presents little resistance to fluid flow.

Figure 3:
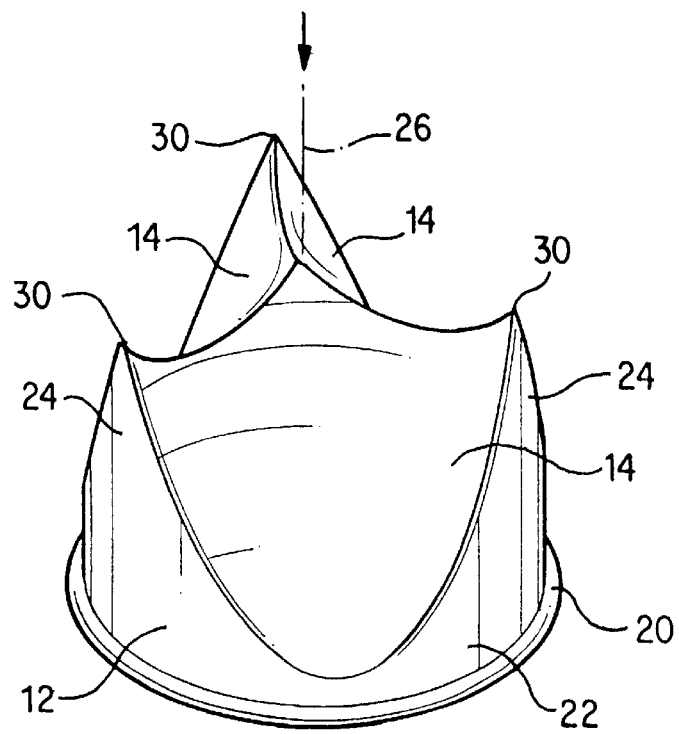
FIG. 3 is a perspective view of a tri-leaflet valve in the closed position.
Figure 4:
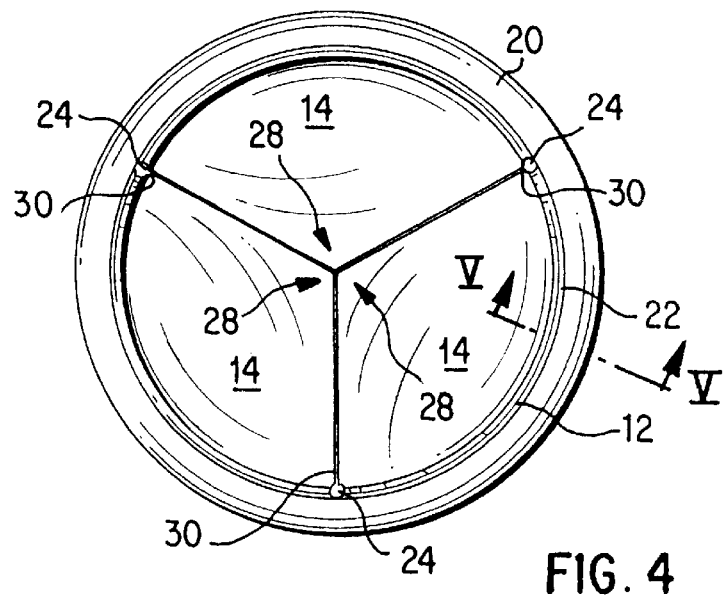
FIG. 4 is a plan view of the valve of FIG. 3.

When fluid flow is in the reverse direction, i.e. in the direction of the arrow shown in FIG. 3, the pressure of the blood flow causes the leaflets to deflect toward axis 26, as shown in FIGS. 3 and 4. In this "closed" position, each leaflet would occlude more than one-third of the valve body's orifice were it not for the presence of the other leaflets. Consequently, when the three leaflets deflect toward axis 26, they engage each other and form coaptive areas that help the valve seal against reverse flow. Further, when the leaflets press together, each leaflet forms a "triple point" 28 at the point where the three leaflets come together, as shown in FIG. 4. The place where the leaflets 14 come together adjacent the posts 24 is called the "commissure" 30, as shown in FIG. 3.

Figure 5:
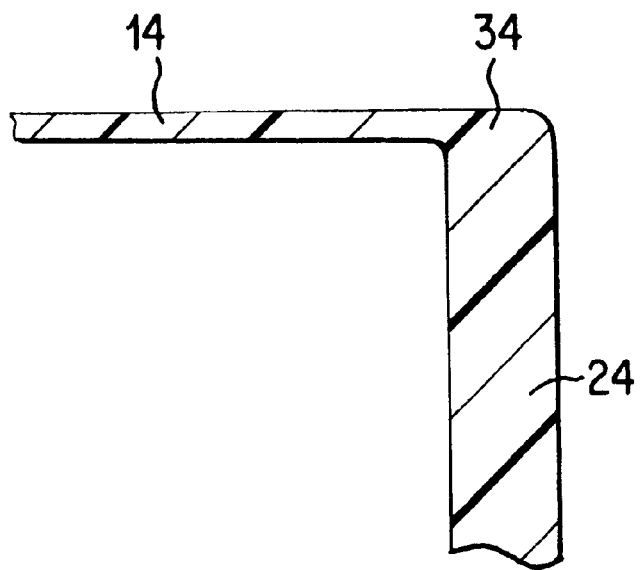
FIGS. 5 and 6 are cross-sectional views along lines V on FIG. 4, showing prior art connections between the leaflet and the valve body.
Figure 6:
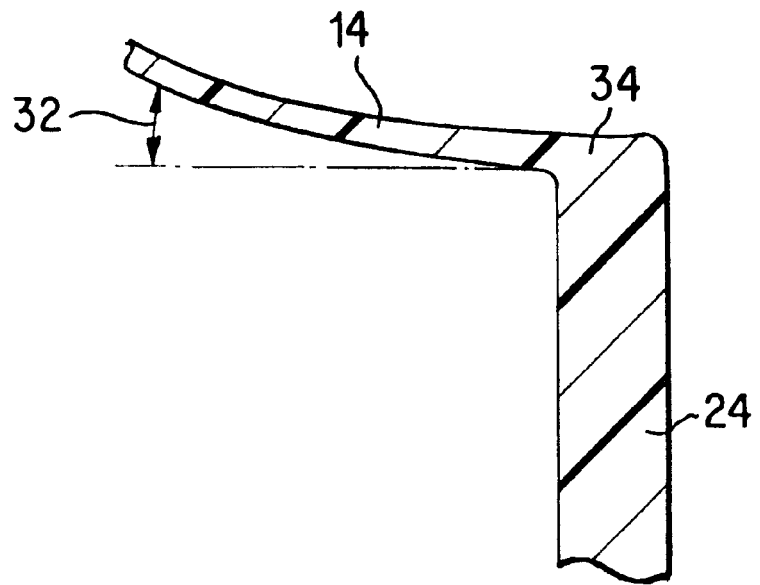

In some prior art tri-leaflet heart valve prostheses, the leaflets 14 were attached to the valve body 12, for example, by stitching. In later designs, however, the leaflets 14 were integrally formed with the leaflet support 24, as shown in FIG. 5. FIG. 5 illustrates a design in which the leaflet 14 is cantilevered from the leaflet support 24. One end of the leaflet 14 is fixed to the leaflet support 24 and the leaflet's free edge (not shown) is free to move. When blood flow causes the leaflet 14 to deflect through an angle 32 as shown in FIG. 6, the displacement and slope of the leaflet at its point of attachment 34 remains zero. Consequently, displacement of other points on the leaflet 14 is accomplished through bending the leaflet 14. In cantilever designs, the thickness of the leaflet 14 is designed to strike a balance between the contradicting requirements of greater thickness for low membrane stress and lesser thickness for low bending stress. The cantilever coupling is structurally continuous and provides no edges or other discontinuities on the blood flow surfaces that could cause eddying or clotting.

Figure 7:
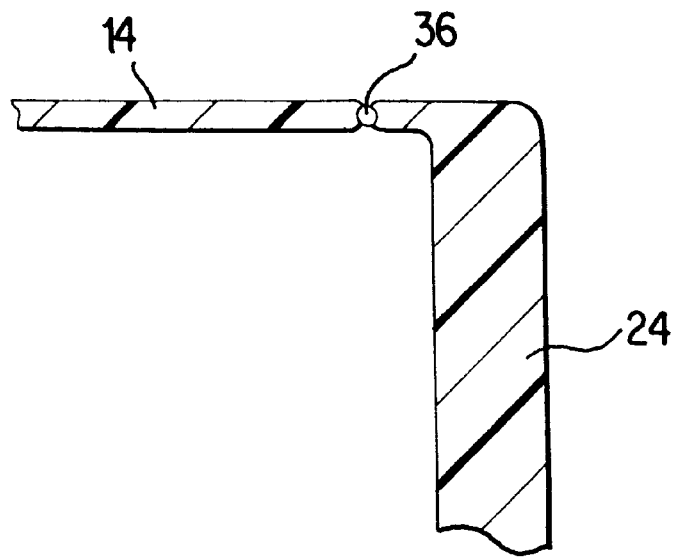
FIGS. 7, 8, 9 and 10 are cross-sectional views along lines V on FIG. 4 showing couplings between the leaflet and the valve body.
Figure 8:
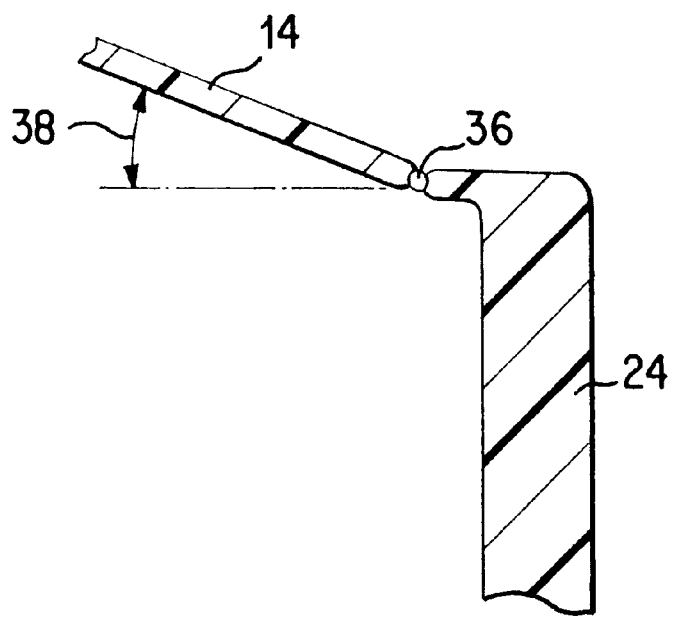

Another approach for coupling the leaflet 14 to the leaflet support 24 is a pivot attachment, as shown in FIG. 7. In a pivot attachment, the leaflet 14 is attached to the leaflet support at a pivot 36. When blood flow causes the leaflet to deflect through angle 38, as shown in FIG. 8, the displacement of the leaflet 14 at the pivot 36 is zero, but the rotation of the leaflet 14 at the pivot 36 is not constrained. Displacements of other points on the leaflet are accomplished through rigid body rotation of the leaflet 14. A pivoting coupling offers less resistance to movement of the leaflet 14 than a cantilever coupling, i.e., it requires less force per unit of displacement of the leaflet 14. Therefore, a heart valve with a pivot coupling has less resistance to opening and a lower forward pressure drop, i.e. pressure differential from one side of the leaflet to the other.

The pivot coupling illustrated in FIGS. 7 and 8 is the type of coupling used in bi-leaflet heart valves. Bi-leaflet valves built with a pivoting coupling between the leaflet 14 and the leaflet support 24 experience less bending stress than the cantilever design described above. Further, pivot coupling designs have small forward pressure drops, which is an important consideration in valve design. The pivot, which is typically assembled from two or more pieces, may produce regions of low flow and may not wash well during valve operation, which can lead to clotting.

Figure 9:
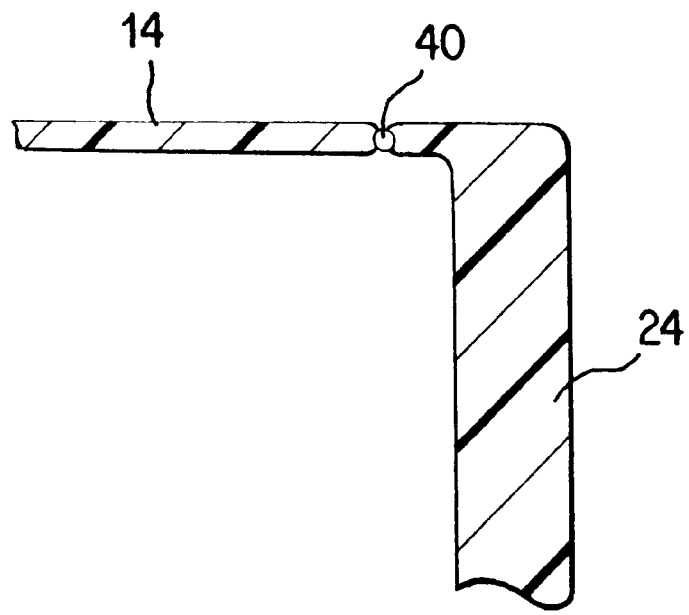
Figure 10:
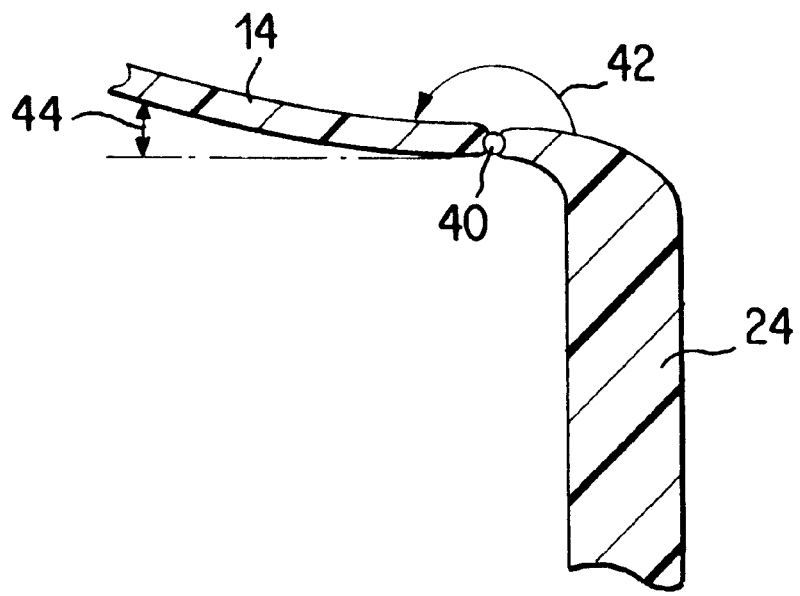

A variation on a pivot coupling is a resisting pivot, as illustrated in FIGS. 9 and 10. Resisting pivots have never been used in tri-leaflet heart valves. Just as in the pivot coupling, the leaflet 14 is coupled to the leaflet support 24 by a pivot 40. Unlike a pivot coupling, however, the resisting pivot 40 exerts a resisting moment 42 when leaflet 14 is deflected by an angle 44. In a resisting pivot, the displacement of the pivot 40 is zero and the slope at the pivot is non-zero but constrained. Further, the leaflet 14 pivots about pivot 40 as a rigid body except for a bending moment that is equal to the rotation resisting moment 42. Like the pivot coupling, the resisting pivot 40 may produce regions of low flow and may not wash well during operation.

Figure 11:
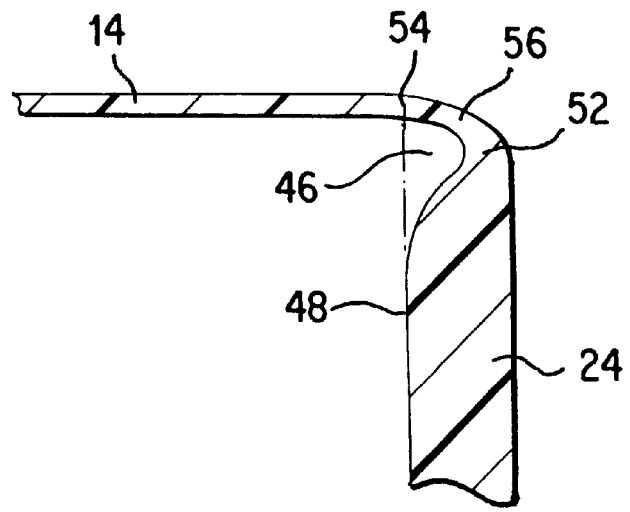
FIGS. 11, 12, 13 and 14 are cross-sectional views along lines V on FIG. 4, showing coupling between the leaflet and the valve body according to the invention.

The invention, illustrated in FIG. 11, uses a living hinge to couple the leaflet 14 to the leaflet support 24. A living hinge is an integral strut cantilevered between two bodies, providing a "virtual pivot" between the two bodies.

Figure 12:
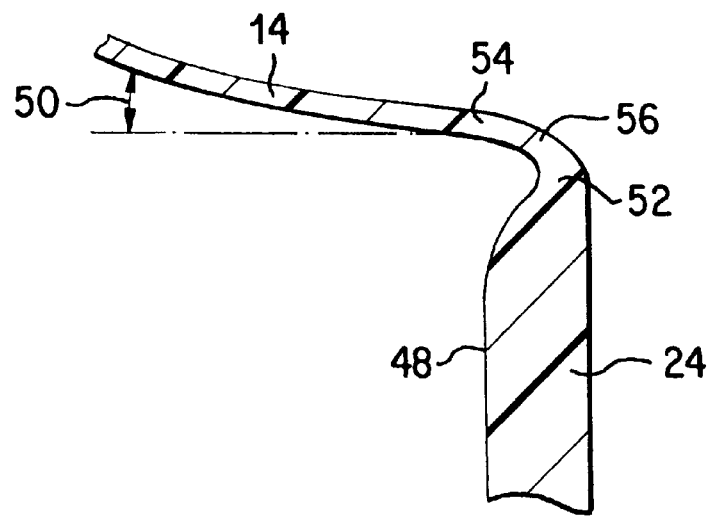

A living hinge, illustrated in FIG. 11, is similar to the cantilever coupling except that material has not been included in the area 46 along the inner diameter 48 of the leaflet support 24. Consequently, when the leaflet is deflected through angle 50, as shown in FIG. 12, the displacement and slope at point 52 remains the same. Point 54 translates upward and the slope of the leaflet at that point is non-zero. This gives the effect of a resistive pivot at point 56, between points 52 and 54. In effect, the region between points 52 and 54 is a "coupling" between the leaflet 14 and the leaflet support 24.

The living hinge experiences less stress than the cantilever design. As discussed above, a cantilever coupling produces bending stresses because the leaflet 14 must bend for the free edge 18 of the leaflet 14 to translate. In contrast, a living hinge acts as a pivot coupling with a small resisting moment, which produces less bending and a smaller bending stress than the cantilever coupling.

The living hinge produces less stagnation and washes better than the true pivot coupling. As discussed above, in the pivot coupling, distinct parts are joined at a pivot with joints and crevices that may produce stagnation and may not wash during operation. In contrast, a living hinge is a single integrated part that has no distinct parts, joints or crevices. The living hinge coupling presents a smooth surface for the flow of blood, as shown in FIG. 12. Thus, the living hinge coupling illustrated in FIGS. 11 and 12 allows the ease of movement associated with the pivot coupling and the structural continuity of a cantilever. Further, because in the living hinge design the leaflet and the leaflet support are integrally attached, they can be fabricated together in a single step using such techniques as injection molding, dip casting, and thermoforming.

Figure 13:
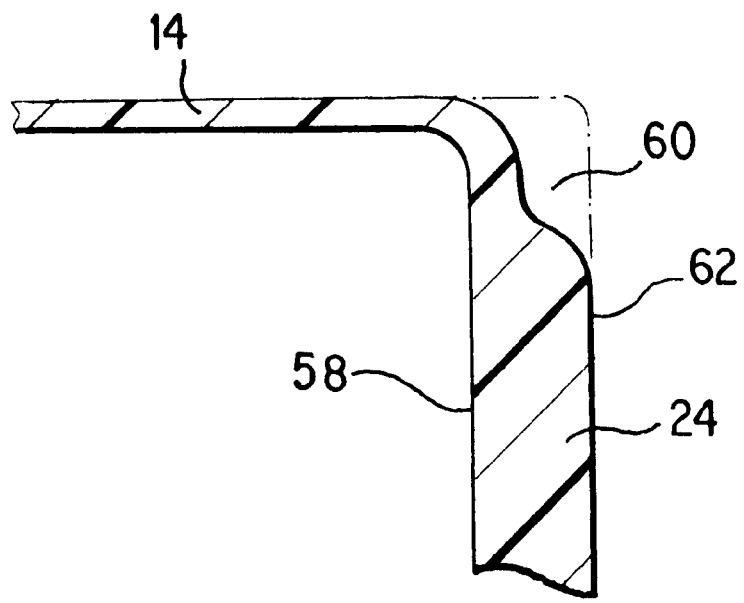

The living hinge illustrated in FIGS. 11 and 12 is coupled to the outer diameter of the leaflet support. Another embodiment, illustrated in FIG. 13, has the living hinge coupled to the inner diameter 58 of the leaflet support 24. This design is similar to the cantilever coupling except that material has not been included in the area 60 along the outer diameter 62 of the leaflet support. This is the preferred embodiment because it provides no recesses for eddying when the leaflet is in the open position.

Figure 14:
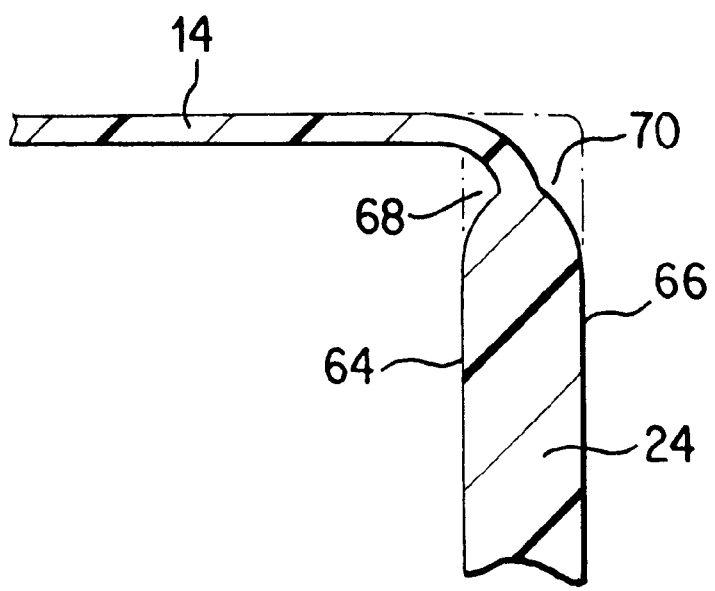

Another embodiment, illustrated in FIG. 14, has the living hinge coupled between the inner diameter 64 and the outer diameter 66. Again, this design is similar to the cantilever coupling except that material has been removed from the areas 68 and 70 along the inner diameter 64 and outer diameter 66, respectively.

The foregoing describes preferred embodiments of the invention and is given by way of example only. For example, while the foregoing describes certain living hinge configurations, the invention encompasses any form of living hinge coupling between a valve body and a leaflet. While the foregoing describes the application of living hinge couplings to tri-leaflet valves, the invention encompasses the application of living hinge couplings to valves having any number of flexible leaflets. Further, the invention is not limited to heart valve technology but is equally applicable to any valve with flexible leaflet occluders. The invention is not limited to any of the specific features described herein, but includes all variations thereof within the scope of the appended claims.

What is claimed is:

1. A prosthetic heart valve comprising:

a valve body having a plurality of leaflet supports;

a plurality of flexible leaflets;

each leaflet support having a first thickness and a reduced thickness portion which is less than the first thickness;

each leaflet connected to a respective leaflet support and having a second thickness which is less than the first thickness; and a living hinge integrally formed with each leaflet support and each leaflet, the living, hinge being a cantilevered member which includes a first portion connected to the reduced thickness portion of the leaflet support, the first portion having a thickness substantially the same as the reduced thickness portion of the leaflet support, and further including a second portion connected to the leaflet, the second portion having a thickness substantially the same as the second thickness of the leaflet.

2. The heart valve of claim 1 wherein each leaflet support includes an inner diameter and an outer diameter, the reduced thickness portion being formed adjacent the inner diameter.

3. The heart valve of claim 1 wherein each leaflet support includes an inner diameter and an outer diameter, the reduced thickness portion being formed adjacent the outer diameter.

4. The heart valve of claim 1 wherein each leaflet support includes all inner diameter and an outer diameter, the reduced thickness portion being formed partially adjacent the inner diameter and partially adjacent the outer diameter.

5. The heart valve of claim 1 wherein the living hinge has a smooth surface.

* * * * *